(12) United States Patent
Freestone et al.

(10) Patent No.: US 6,649,398 B2
(45) Date of Patent: *Nov. 18, 2003

(54) METHOD FOR INDUCING BACTERIAL GROWTH USING AUTOINDUCERS

(75) Inventors: Primrose Pamela Elaine Freestone, Leicester (GB); Peter Humphrey Williams, Leicester (GB); Mark Lyte, Eagan, MN (US); Richard David Haigh, Leicester (GB)

(73) Assignee: University of Leicester, Leicester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,291

(22) Filed: Jul. 12, 2001

(65) Prior Publication Data

US 2002/0068330 A1 Jun. 6, 2002

Related U.S. Application Data

(62) Division of application No. 09/424,427, filed on Feb. 28, 2000, now Pat. No. 6,316,244.

(30) Foreign Application Priority Data

May 22, 1997 (GB) .............................................. 9710497
May 22, 1998 (GB) ................................. PCT/GB98/01395

(51) Int. Cl.$^7$ .......................... A01N 63/00; C12N 1/00; C12N 1/12; C12N 1/20

(52) U.S. Cl. .................. 435/252.1; 424/93.4; 424/780; 435/243; 435/252.8; 435/822; 435/849; 435/879

(58) Field of Search .............................. 435/252.1, 822, 435/93.4, 780, 243, 252.8, 849, 879

(56) References Cited

U.S. PATENT DOCUMENTS 6,316,244 B1 * 11/2001 Freestone ................ 435/252.1

* cited by examiner

*Primary Examiner*—David M. Naff
*Assistant Examiner*—Deborah K. Ware
(74) *Attorney, Agent, or Firm*—Bracewell & Patterson LLP

(57) ABSTRACT

A bacterial autoinducer and method for isolating and purifying a bacterial autoinducer form a sample comprising the steps of collecting a sample containing the autoinducer, fractionating the sample to isolate fractions corresponding to molecular weights of approximately 300–1500 Dalton, and eluting the isolate on an anion-exchange chromatographic column and selecting the faction containing the autoinducer.

12 Claims, 12 Drawing Sheets

METHOD FOR INDUCING BACTERIAL GROWTH USING AUTOINDUCERS

CROSS-REFERENCE TO RELATED APPLICATIONS

This application is a divisional and claims benefit of priority of U.S. patent application Ser No. 09/424,427, filed Feb. 28, 2000, now U.S. Pat. No. 6,316,244.

BACKGROUND

1. Field of the Invention

The present invention concerns bacterial autoinducers of growth, methods for their purification, autoinducers purified by such methods, and their use to induce the growth of bacteria, both the source organism and other species.

2. Description of the Related Art

Signalling events between bacteria and host cells are an integral component of the dynamic and complex process of infection and disease. It has recently become clear that signalling between bacteria is also of importance to this process.

Low molecular weight, diffusible signal molecules produced by bacteria, termed autoinducers (AI), play a crucial role in the development of bacterial infections, of both plants and animals. These autoinducers may determine whether or not an initial infection, often involving only a very few bacteria, will succumb to the many defence mechanisms of a host or whether these host defences are overcome, and bacterial growth and disease occur.

One class of autoinducers has already been well-characterised, the N-acyl homoserine lactones, which are composed of derivatives of amino acid and fatty acid molecules. This family of molecules play a key role in the mechanisms by which Gram negative bacteria monitor population densities, factors which are important in virulence of a number species. However, despite the fact that N-acyl homoserine lactone-type sensing systems have been shown to exist in *E. coli*, there is so far no evidence that N-acyl homoserine lactones themselves are made by, or play a role in the pathogenesis of this organism. In addition, no evidence has been so far been presented to suggest a role for these autoinducers in the pathogenensis of Salmonella.

The existence of an additional class of autoinducer molecule has been shown, the AI being different from the homoserine lactones. These also appear to play an important role in pathogenesis.

A purported bacterial AI was isolated by Lyte, M. et al. (1996, FEMS Microbiology Letters, 139: 155–159) having a molecular weight of approximately 10,000 Da (see also, Lyte, M., 1993, Journal of Endocrinology, 137: 343–345; U.S. Pat. No. 5,629,349).

BRIEF SUMMARY OF THE INVENTION

The present inventors have succeeded in isolating, purifying and characterising a novel autoinducer from *E. coli* and *Hafnia alvei*.

According to the present invention there is provided a bacterial autoinducer, characterised in that it has substantially the following properties:

i) it is produced in response to noradrenaline in serum SAPI medium;
ii) it is heat stable;
iii) it is stable to lyophilisation;
iv) it has a negative charge;
v) it is polar;
vi) it is hydrophilic;
vii) it will not partition into organic solvents;
viii) it is capable of binding positively charged metal ions; and
ix) it has a molecular weight of about 300–1500 daltons The bacterium may be *E. coli* or *Hafnia alveii*.

The bacterium may be Salmonella, for example *S. enteriditis* or *S. typhimurium*.

The autoinducer is distinct from N-acyl homoserine lactones and the molecule of Lyte et al. (1996, supra) (for example, the molecular weight of an autoinducer according to the present invention is less than 1000 Da, compared to the 10,000 Da of Lyte et al.). Similarly it is not a peptide pheremone nor is it a known siderophore such as enterochelin which, amongst other things, is stable to acidification, soluble in organic solvents such as ethanol and upon crystallisation forms white needle-like crystals. Experiments (below) show that the autoinducers of the present invention appear to form a novel family of highly-related molecules.

The autoinducer has a wide range of possible uses, essentially including anything in which the growth of a bacterium or the production of a desired molecule is to be stimulated or assayed. For example, it may be used in fermentation processes, in culture media for diagnostic and environmental monitoring or in the drug discovery process in order to find agents which will inhibit autoinducer-mediated bacterial stimulation. In fermentation processes, the autoinducer may be used to stimulate starting cultures or to shorten and synchronise lag phases; in fermentation processes to stimulate the production of secondary metabolites such as antibiotics, chemicals for biological screening, and recombinant proteins; in culture media to shorten turnaround times or to assay viable but non-culturable organisms. Other uses of the autoinducer will be readily apparent to one skilled in the art.

The *E. coli* autoinducer is a low molecular weight diffusible signal molecule, initially found as a bacterial response to physiologically relevant concentrations of noradrenaline, such as those found in the gastrointestinal tract of mammalian hosts. This effect is not nutritionally mediated. The half-life of activity of intestinal nor-adrenaline is quite short lived—the hormone is active for only a few hours, before becoming irreversibly sulphonated. However, this transient exposure to nor-adrenaline is sufficient to induce the bacteria to synthesize their own growth stimulus, the autoinducer, which has much greater stability. The autoinducer acts by effecting both accelerated growth rate, increased bacterial cell numbers and the production of virulence factors, such as toxins and adhesins, the activity being cross-species specific.

The apparent molecular weight of the *E. coli* autoinducer is dependent upon the elution conditions used (see 'Experimental' below), due to the substantial charge the molecule has. Experiments (below) have shown the charge on the molecule to be greater than that on ATP. The molecule has also been found to be polar. It is heat stable and is capable of being autoclaved at 121° C. Similarly it is capable of withstanding lyophilisation. The molecule is also capable of inducing cross-species stimulation.

The above list of characteristics may be considered the "core" characteristics of the family of autoinducers. Other characteristics have been identified as detailed in the experimental section below and the autoinducer may have at least one of the following characteristics:

i) it has absorbtion maxima at 255,325 and 500–550 nm; and ii) it is stable in prolonged storage in a dried state and/or in solution.

Additional characteristics (which may be specific to the *E. coli*, *Salmonella* or *Hafnia* autoinducers) of which the autoinducer may have at least one are:

i) it is produced in substantially smaller quantities by bacteria grown in LURIA broth, Tryptone soya broth, M9 minimal medium and Davis-Mingioli minimal medium than by the same bacteria grown in serum SAPI medium;

ii) it has a reddish-pink colour, reversibly decolorisable by reducing the pH to <4;

iii) it contains serine;

iv) its synthesis involves the entA and entB gene products;

v) its synthesis is not stimulated by conditions of Fe starvation;

vi) it is synthesised in conditions of excess Fe;

vii) its entry into bacteria occurs via a tonB dependent receptor;

viii) it is inactivated by oxidation;

ix) it is inactivated by extreme pH; and x) it is resistant to degradation by ribonuclease, deoxyribonuclease, trypsin, pepsin, V8 protease, proteinase K, acid phosphatases, alkaline phosphates and phosphodiesterase.

Also provided according to the present invention is a method for isolating and purifying a bacterial autoinducer from a sample comprising the steps of:

i) collecting a sample containing the autoinducer;

ii) fractionating the sample to isolate fractions corresponding to molecular weights of approximately 300–1500 Daltons; and iii) eluting the isolate of (ii) on an anion-exchange chromatographic column and selecting the fraction containing the autoinducer.

It may comprise the additional step of performing gel filtration chromatography upon the fraction containing the autoinducer selected in (iii) and selecting the fraction containing the autoinducer.

It may comprise the additional step of concentrating the sample prior to fractionation.

Concentration may be achieved by means of ultrafiltration. Such ultra-filtration may be performed with a membrane molecular weight cut-off (MWCO) of approximately 100 Daltons. Alternatively, concentration maybe by means of lyophilisation or filtration or a combination thereof.

The sample may be collected from a culture containing bacteria and the autoinducer. It may be a supernatant collected from a centrifuged culture containing bacteria and the autoinducer.

Fractionation may be by means of size exclusion gel filtration.

Size exclusion gel filtration maybe performed using a buffer of approximately 100 mM ammonium bicarbonate, pH 8.0, anion exchange purification being performed on an anion exchange column with a triethylammonium bicarbonate gradient.

Alternatively, size exclusion gel filtration may be performed using a buffer of approximately 20 mM potassium phosphate containing 150 mM NaCl, pH 7.4, anion exchange purification being performed on an anion exchange column with a NaCl gradient.

Size exclusion separation of the autoinducer may also be performed using preparative ultrafiltration with a MWCO greater than that of the autoinducer, for example 1500 Da.

Other conditions for performing anion-exchange purification and concentration of the sample will be readily apparent to one skilled in the art, particularly with regard to the highly distinctive physical characteristics of the autoinducer.

Also provided according to the present invention is a bacterial autoinducer isolated and purified according to the method of the invention.

Also provided according to the present invention is the use of a bacterial autoinducer according to the present invention in inducing bacterial growth, the production of bacteria toxins or the production of bacterial adhesins. The use may of course be with bacteria of the species from which the autoinducer was derived, or of another species.

BRIEF DESCRIPTION OF THE DRAWINGS

The invention will be further apparent from the following description, with reference to the several figures of the accompanying drawings, which show, by way of example only, forms of bacterial autoinducers. Of the figures:

FIG. 6c shows effects of autoinducers from (top) *Yersinnia entercolitica*, (middle) *Pseudomonas aeruginosa* and (bottom) *Morganella morganii*. Axes as for FIG. 6a;

FIG. 6d shows effects of autoinducers from (top) *Salmonella enterica* Sv. Enteriditis, (middle) *Enterococcus faecalis* and (bottom) *Enterococcus faecium*. Axes as for FIG. 6a;

FIG. 6e shows the effect of *Staphylococcus albus* autoinducer. Axes as for FIG. 6a;

DETAILED DESCRIPTION OF THE INVENTION

Figure 1:
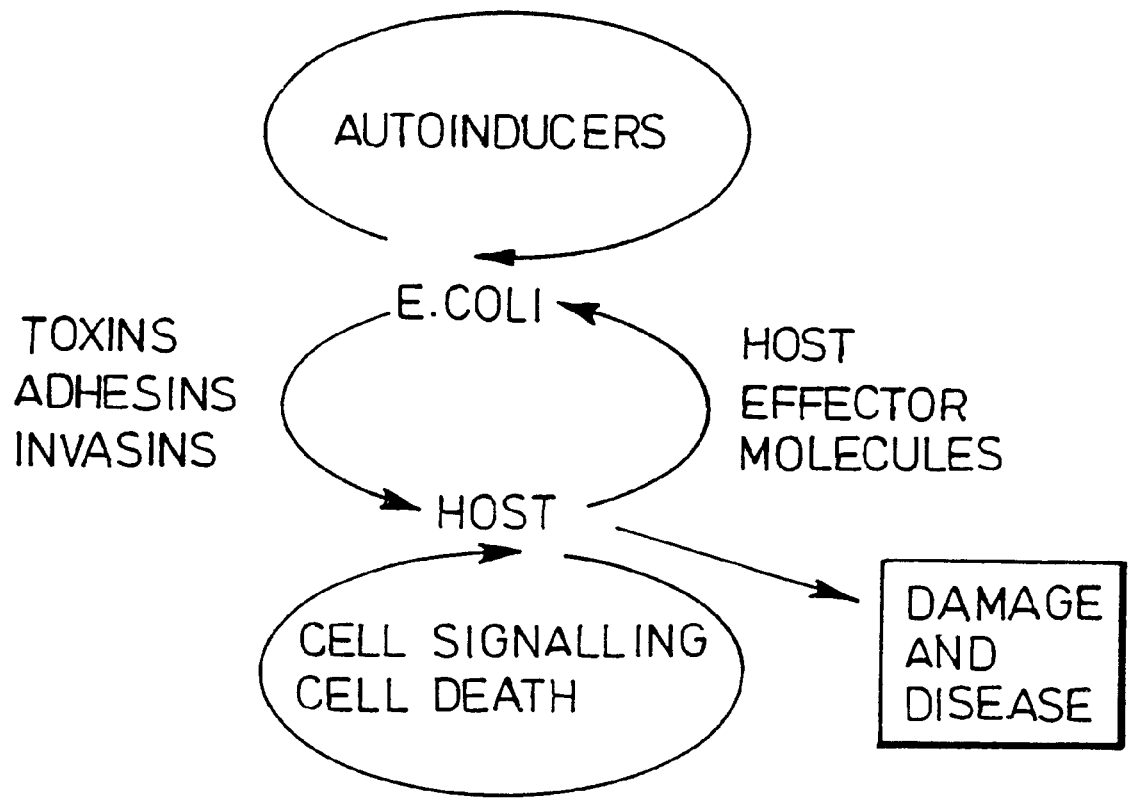
FIG. 1 shows the role of host and bacterial cellular signalling molecules in the pathogenesis of bacterial infectious diseases.

As can be seen from FIG. 1, recognition of host effector molecules (such as hormones, eg noradrenaline) are used by the bacteria (in this case, *E. coli*) to detect that they are within a suitable host. Bacteria respond to host effectors by the production of virulence factors (toxins, adhesins and invasins), toxic proteins which allow them to invade cells and so establish and spread infection. These virulence factors can activate signalling pathways in host cells, which can lead to cell death and tissue damage. If the damage caused by the bacteria is sufficient, the host experiences symptoms of disease Not only is signalling between host and bacteria important, but also signalling between bacteria, via low molecular weight diffusible molecules called autoinducers. These allow the expression of the genes which encode virulence factors to be coordinated to optimum bacterial population densities.

The experiments below detail the isolation and purification of autoinducers from *E.coli* and *Hafnia alvei*, together with studies of the effects of these and other autoinducers upon bacteria (both gram-negative and gram-positive) of the same and other species which show that the bacterial autoinducer of the present invention is capable of effecting signalling between different species of bacteria.

The experiments also detail the characterisation of the physical characteristics of the *E.coli* autoinducer and the autoinducers of other species and show that the autoinducers form a family of similar molecules, which may be isolated and purified using the same basic purification strategy—for example, the autoinducer of *Hafnia alvei* was isolated and purified using the same strategy as that employed for the *E.coli* autoinducer.

Extraction and Purification

*E.coli* O157:H7 were cultured as follows:

Bacteria (approximately 50–500 cfu/ml) are inoculated into SAPI minimal medium (6.25 mM $NH_4NO_3$, 1.84 mM $KH_2PO_4$, 3.35 mM KCl, 1.01 mM $MgSO_4$ and 2.77 mM glucose, pH 7.5) supplemented with 30% (v/v) adult bovine serum (Sigma), and either 1% (v/v) previously made *E.coli* autoinducer or 50 mM norepinephrine.

The cultures are grown statically (i.e. without aeration by shaking) for 24 hours at 37° C. in a 5% $CO_2$ incubator.

The bacteria are pelleted by centrifugation, and culture supernatants containing the autoinducer are sterilised by filtration through a 0.2 $\mu$m pore diameter filter.

Purification

Figure 2:
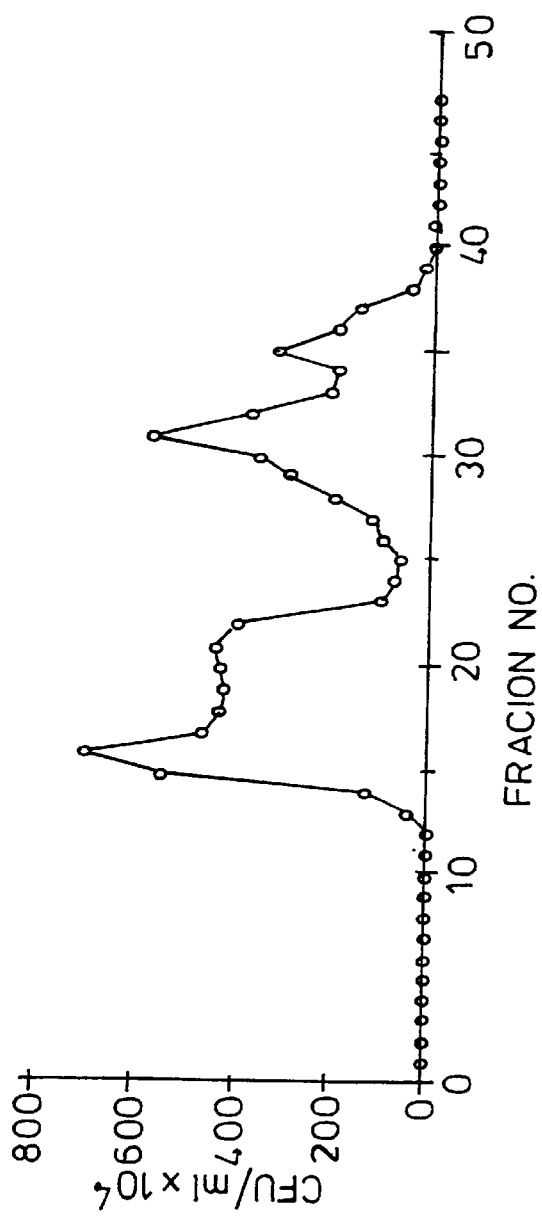
FIG. 2 shows Step 1 of the chromatographic purification of the *Escherichia coli* autoinducer. Superdex 30 gel filtration elution profile of concentrated AI equivalent to 125 ml of unpurified supernatant. Top graph, Y-axis: AI activity in fractions expressed as CFU/ml (colony forming units/ml× $10^4$); X-axis, fraction number (8 ml fractions). Bottom graph, Y-axis: 280 nm UV absorbance elution profile (100% mark=absorbance of 1.0); X-axis, fraction number (8 ml fractions)
Figure 2:
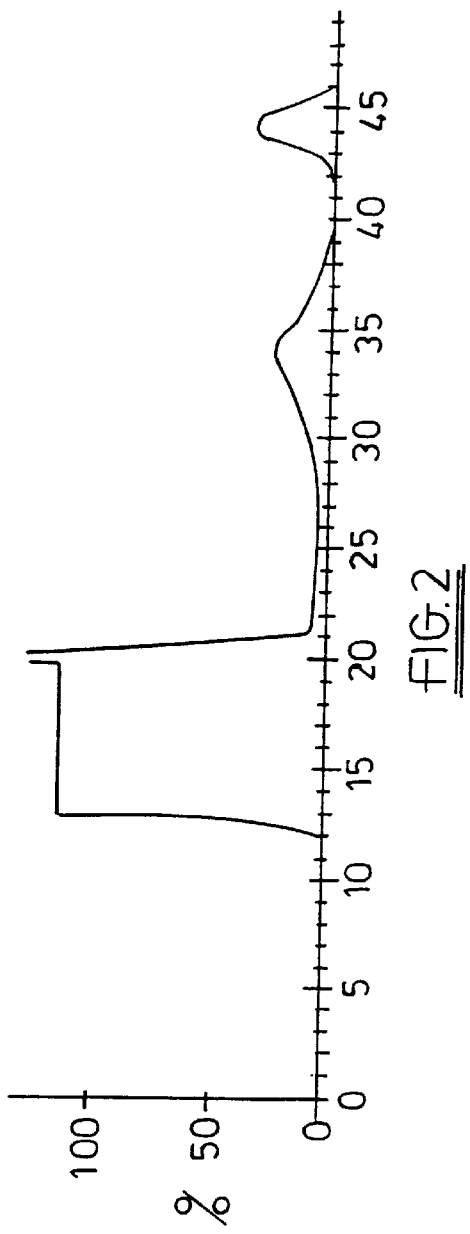

Purification of the autoinducer from the bacterial culture (above) was performed as follows:

Step 1—Superdex 30 Gel Filtration Chromatogaphy (FIG. 2)

The filter-sterilised culture supernatants are lyophilised, dissolved at $\frac{1}{7}$ their original volume in distilled water, and re-filtered. 20 ml aliquots of ×8-concentrated material are then fractionated by gel filtration (size exclusion) chromatography on a Superdex 30 (prep grade) column (2.6×65 cm, total volume 360 ml) connected to a Pharmacia FPLC. The column is run at a flow rate of 1.5 ml/min, and the chromatography buffer is 100 mM ammonium bicarbonate, pH 8.0. This was chosen because it is volatile; the use of other buffers is possible at this stage of the purification, provided they contain no more than 200 mM Na/KCl (higher concentrations may affect autoinducer binding to the Mono P column in the next stage).

The total activity of the crude autoinducer is roughly equally divided between two major peaks of activity. One represents a serum protein-bound form of the autoinducer (corresponding to the huge UV absorbance peak on the A280 profile). This was proved by heat treatment of the high molecular weight fractions in the presence of NaCl; subsequent molecular weight analysis (gel filtration) showed disappearance of the high molecular weight peak, and the appearance of a low molecular weight peak of autoinducer activity. Similarly, when whole autoinducer preparations were heat-treated in the presence of NaCl the high molecular weight peak disappeared, with a corresponding increase in the size of the low molecular weight peaks. The molecule bound by the autoinducer has a molecular weight of around 10 kDa, and is definitely not BSA (approximately 67–70 kDa).

The low molecular weight activity is the material used for further purification. We consistently observe two broad peaks, corresponding to molecular weights of around 600 and 400 Da. The extreme electronegativity of the autoinducer may cause it to interact with the gel filtration column in a charge-mediated manner so causing it to run aberrantly. However, gel filtration in the presence of elevated NaCl (0.5 M as opposed to the usual 0.15 M) does not abolish the 2-peak profile of the low molecular weight material. The heterogeneity of this activity may represent interactions of autoinducer molecules with one another and/or with other components of the serum medium.

Figure 3:
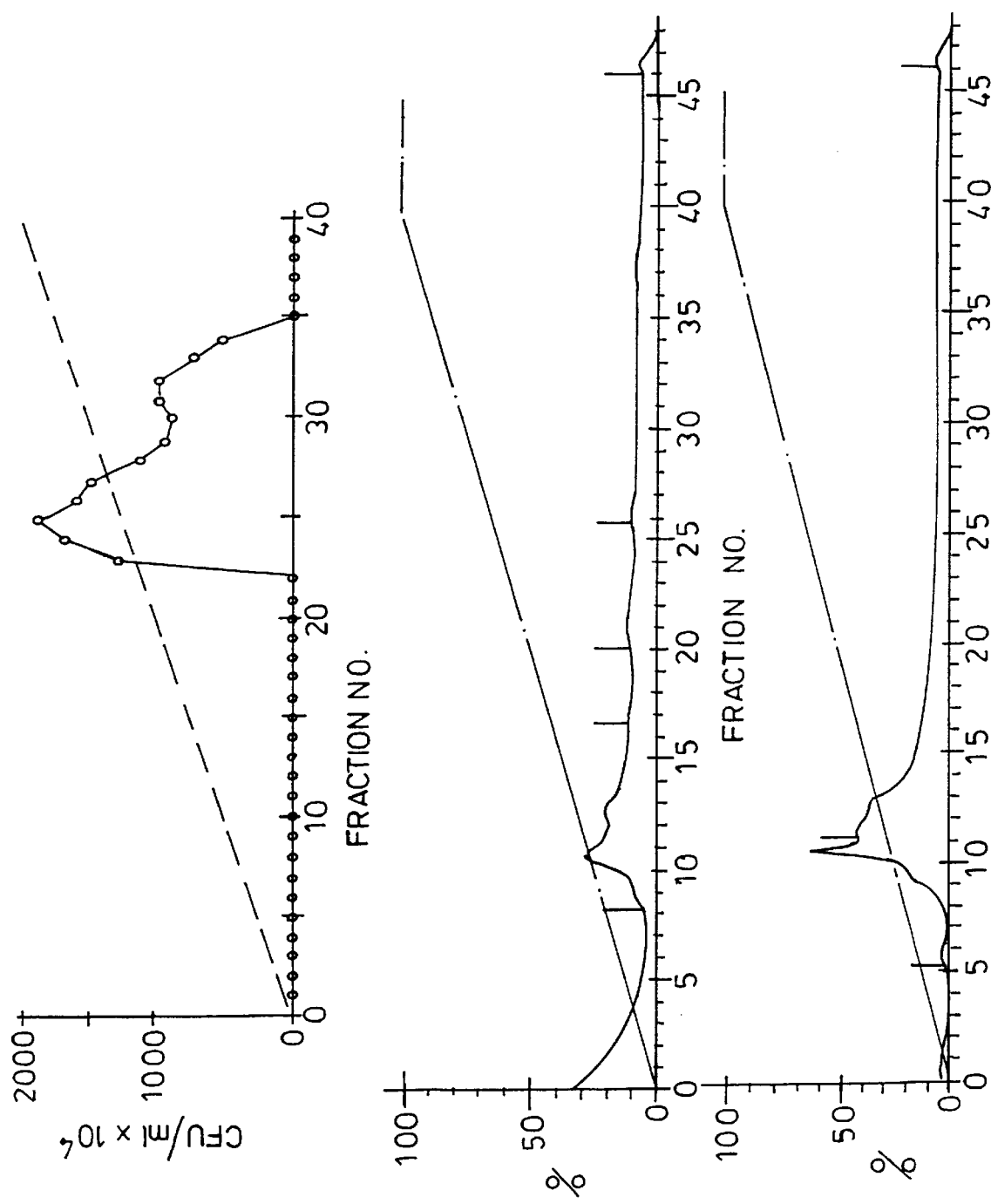
FIG. 3 shows Step 2 of the chromatographic purification of the *Escherichia coli* autoinducer. Mono P anion exchange elution profile of 250 ml of Step 1 -purified *Escherichia coli* autoinducer. Top graph, Y-axis: AI activity in Mono P fractions expressed as CFU/ml (colony forming units/ml× $10^4$); X-axis, fraction number (1 ml fractions). Middle graph, Y-axis: 280 nm UV absorbance elution profile of a Step 1-purified sample containing AI (100% mark= Absorbance of 0.5); X-axis, fraction number (1 ml fractions). Bottom graph, 280 nm UV absorbance elution profile of a Step 1-purified production medium sample without AI i.e. negative control (100% mark=absorbance of 0.5); X-axis, fraction number (1 ml fractions)

Step 2—Mono P Anion Exchange Chromatography (FIG. 3)

The pooled fractions from 2 Superdex separations are further purified using a 1 ml Pharmacia Mono P 5/5 column, equilibrated in 20 mM triethylammonium bicarbonate (TEAB) buffer, pH 7.5. The autoinducer is isolated using a 40 ml gradient of 20 to 1000 mM TEAB. The autoinducer elutes between 500 and 700 mM TEAB. Concentration of the Mono P autoinducer fractions (approximately 10 ml) and removal of the TEAB buffer is achieved by lyophilisation; the pooled fractions are lyophilised, redissolved in distilled water, and re-lyophilised.

Mono P is a very weak anion exchanger (it is normally used for chromatofocussing), and it was chosen because of the high degree of electronegativity of the autoinducer, and the consequent problems of its elution from moderate or strong anion exchangers.

TEAB is a volatile salt which is therefore easily removed by lyophilisation (although note that concentrations of TEAB up to 20 mM are not inhibitory in the growth stimulation assays).

Stronger anion exchange columns could be used, but the extreme electronegativity of the autoinducer causes it to bind with high affinity to moderate or strong anion exchangers, and high concentrations of non-volatile salts such as NaCl or KCl (1–2 M) are then required for elution.

The strategy of reducing pH to reduce electronegativity in order to reduce the salt required for elution does not work with our molecule. Indeed, removing salt from a molecule the size of our autoinducer is extremely difficult.

The activity profile of the Mono P column fractions shows two peaks of activity, indicating two (negatively) charged states. We have also observed that autoinducer is inactivated by oxidation; treatment with 100 mM $H_2O_2$, followed by lyophilisation to remove the oxidant, causes a 20-fold reduction in activity of the autoinducer in 1 hour and total loss of activity in 4.5 hours. The peroxide effect is also concentration-dependent.

Figure 4:
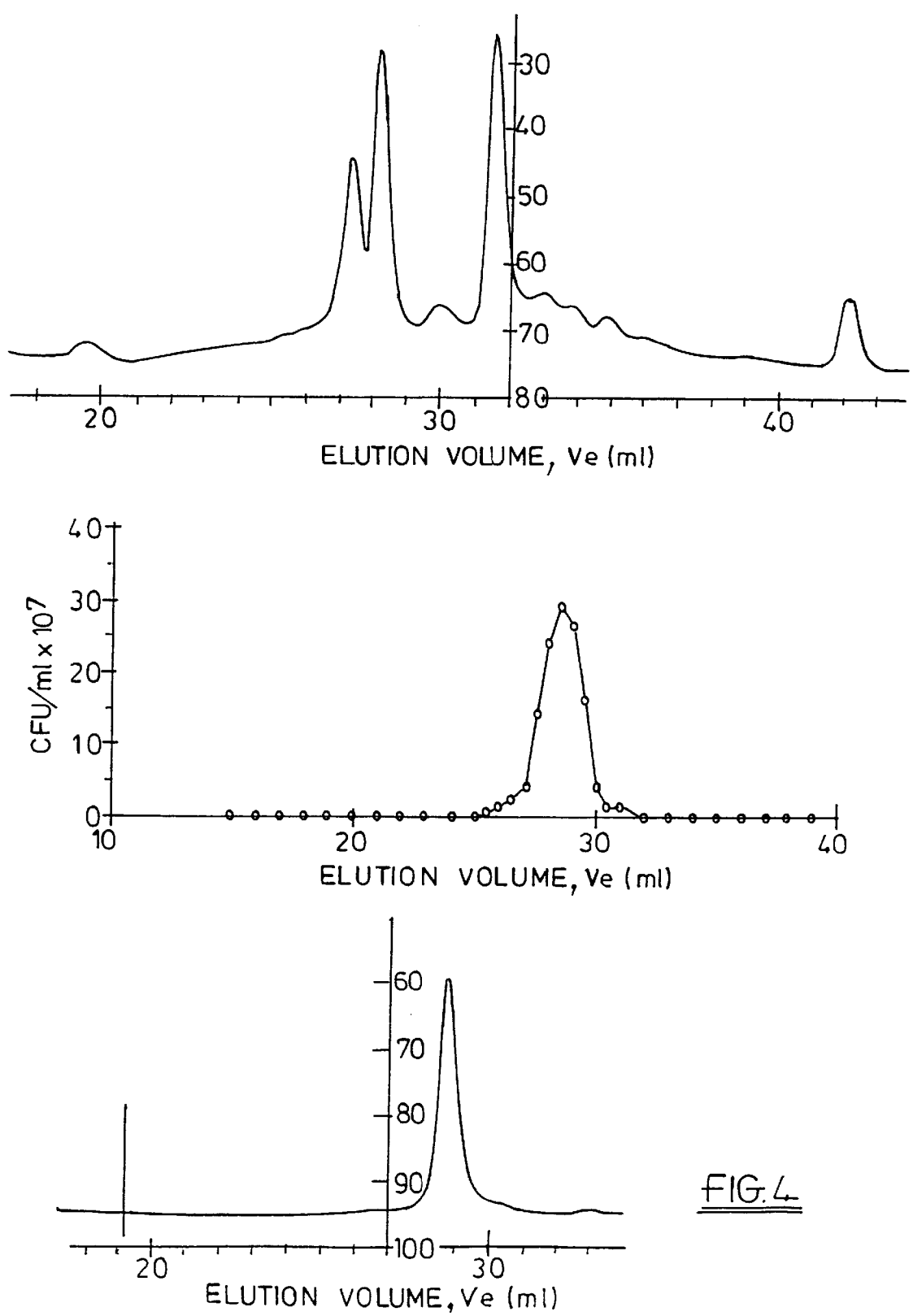
FIG. 4 shows Step 3 of the chromatographic purification of the *Escherichia coli* autoinducer. Superdex peptide gel filtration elution profile of the *Escherichia coli* autoinducer. Top graph, 280 nm UV absorbance elution profile of 5 ml of Step 2-purified AI concentrated to 50 $\mu$l. Y-axis: (100% mark=absorbance of 0.2); X-axis, elution volume, $V_e$, ml. Middle graph: AI activity in Mono P fractions expressed as CFU/ml (colony forming units/ml× $10^4$ ); X-axis, fraction number (1 ml fractions). Bottom graph, 280 nm UV absorbance elution profile showing refractionation of Step 3-purified AI peak (2.5 ml of peak eluting at approx. 28.5 ml, concentrated to 50 $\mu$l). Y-axis: 280 nm UV absorbance elution profile (100% mark=absorbance of 0.2); X-axis, elution volume, $V_e$, ml.

Step 3—Superdex Pep Gel Filtration Chromatography (FIG. 4)

AI-containing fractions from one Mono P fractionation (approx 10 ml) are pooled, concentrated by one lyophilisation, re-dissolved in 100 ml of 200 mM TEAB buffer, and fractionated in 50 ml aliquots on two Pharmacia Superdex peptide HR 10/30 anaytical columns connected in series (effective column dimensions 1.0×60 cm, total volume 48 ml). The columns are equilibrated in 200 mM TEAB, and run at a flow rate of 0.4 ml/min.

The autoinducer activity elutes as a single, discrete peak (1.5–2 ml) with an average $V_e$ of 28.5 ml. To achieve further purification, peak AI fractions are pooled, concentrated by lyophilisation, and refractionated as described above. If necessary, final 'polishing' (i.e. purification) is achieved by a third fractionation. Symmetrical autoinducer peaks are pooled, extracted three times with chloroform:isoamyl alcohol (24:1) to remove possible residual traces of polyethylene glycol (an occasional contaminant from the commercially prepared serum used in our production medium) and lyophilised to remove TEAB buffer as described above.

The symmetry of the UV absorbance and activity peaks of the Step 3-purified autoinducer and the results of various forms of MS analysis (see below) suggest that our preparation has been purified to a level approaching homogeneity.

The purification scheme (above) is highly reproducible and a typical AI purification starting with 800 ml of culture supernatant produces approximately 0.1–0.2 mg (dry weight) of Step 3 autoinducer. We estimate that the effective concentration of this material is in the micromolar to nanomolar range, indicating that the growth stimulatory effects of the autoinducer are not simply due to its use as a source of nutrition.

Experiments performed with an $E.$ $coli$ mutant unable to respond to nor-epinephrine or to synthesize autoinducer, show that autoinducer is actively withdrawn from media during growth, and that the extent of growth is determined by the availability of autoinducer.

The protocol described here (see also Table 1, below) involves a complex protein-rich culture medium which limits the efficiency of the initial gel filtration, making it very time-consuming.

It has been found that a fur mutant (i.e. derepressed for iron-responsive genes) of $E.$ $coli$ K-12 (strain H1780) appears to constitutively express substantial levels of a heat-stable autoinducer-like activity under non-inducing growth conditions such as the rich medium Tryptic Soya Broth (TSB) and, crucially, M9 minimal medium lacking serum supplementation.

However, addition of iron chelators such as a, a'-dipyridyl to TSB in order to derepress iron-responsive genes does not result in increased production of autoinducer activity by wild-type (i.e. $fur^+$) strains.

Moreover, various clinical isolates of $E.$ $coli$ produce heat-stable autoinducer-like activity in standard M9 minimal medium, although at somewhat lower levels than in the conditions described previously. Preliminary examination of the chromatographic, UV/visible, and ESMS properties of this autoinducer-like activity suggest that it is very similar, if not identical, to the autoinducer made (above) using serum-based media.

The advantages of production of autoinducer in a simple, protein-free minimal medium are enormous, in terms both of cost and of the speed and simplicity of the purification protocol. Scaling-up is simple to achieve and, with constitutive expression by the fur mutant, continuous fermenter culture is also a possibility.

Characteristics

Stability (see also Table 2)

The $E.$ $coli$ autoinducer is a very stable molecule. It is especially resistant to heat inactivation, and can even be autoclaved without losing activity. In its unpurified form it is stable to prolonged storage in solution, without any loss of growth stimulatory activity. It is also stable to lyophilisation, and to storage in a dry powder form for at least a year.

The autoinducer is normally stored at −20° C. as a preventative measure, since we have shown that the purified molecule is inactivated by oxidation. However, autoinducer is stable to storage either dried or in solution for at least 4 months at 4° C. The molecule is also stable to storage at room temperature for at least 6 weeks.

The autoinducer is rapidly and irreversibly inactivated at extreme pH values.

Autoinducer production in other bacterial pathogens (see also Table 4, FIGS. 5, 6A–6E)

The autoinducer produced by $E.$ $coli$ also stimulates growth of a range of other bacteria, including many members of the family Enterobacteriaceae, as well as other Gram negative and Gram positive species (Table 4).

Figure 5:
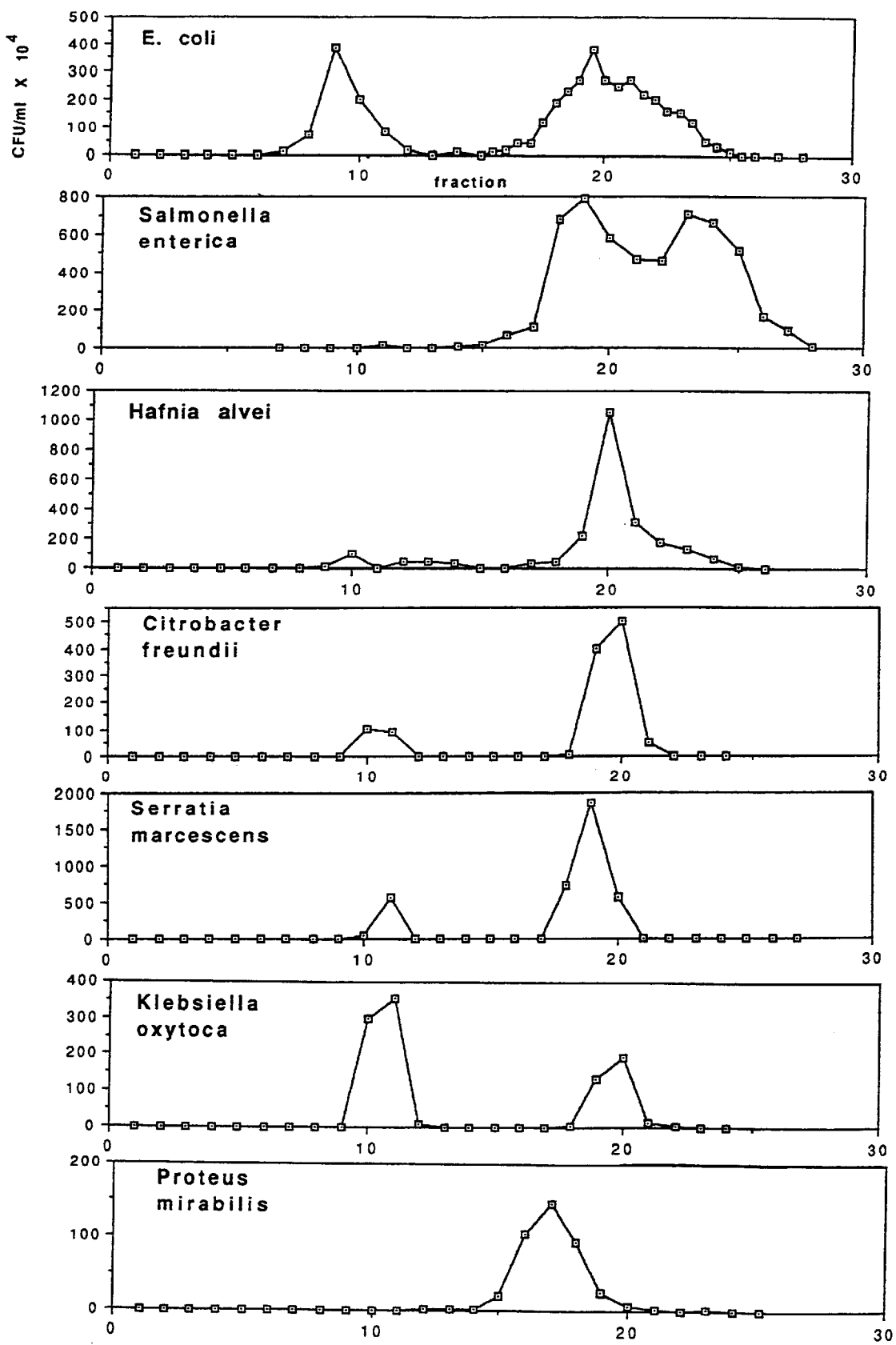
FIG. 5 shows the Superdex 75 gel filtration elution profiles of novel autoinducers. Plots are for Plots are for (top-bottom) *E. coli, Salmonella enteriditis, Citrobacter freundii, Serratia marcescens, Klebsiella oxytoca* and *Proteus mirabilis*. Y-axis shows the AI activity profile per fraction (CFU/ml× $10^4$); X-axis shows fraction number (1 ml fractions) [equivalent to elution volume, $V_e$, ml]. The first peak of activity around fraction 10 shows autoinducer bound to a serum protein; the later peaks (around fraction 20) show the free AI molecules. With the esception of the Proteus AI (around 1500 Da), these are of roughly similar molecular weights (less than 1000 Da).
Figure 6A:
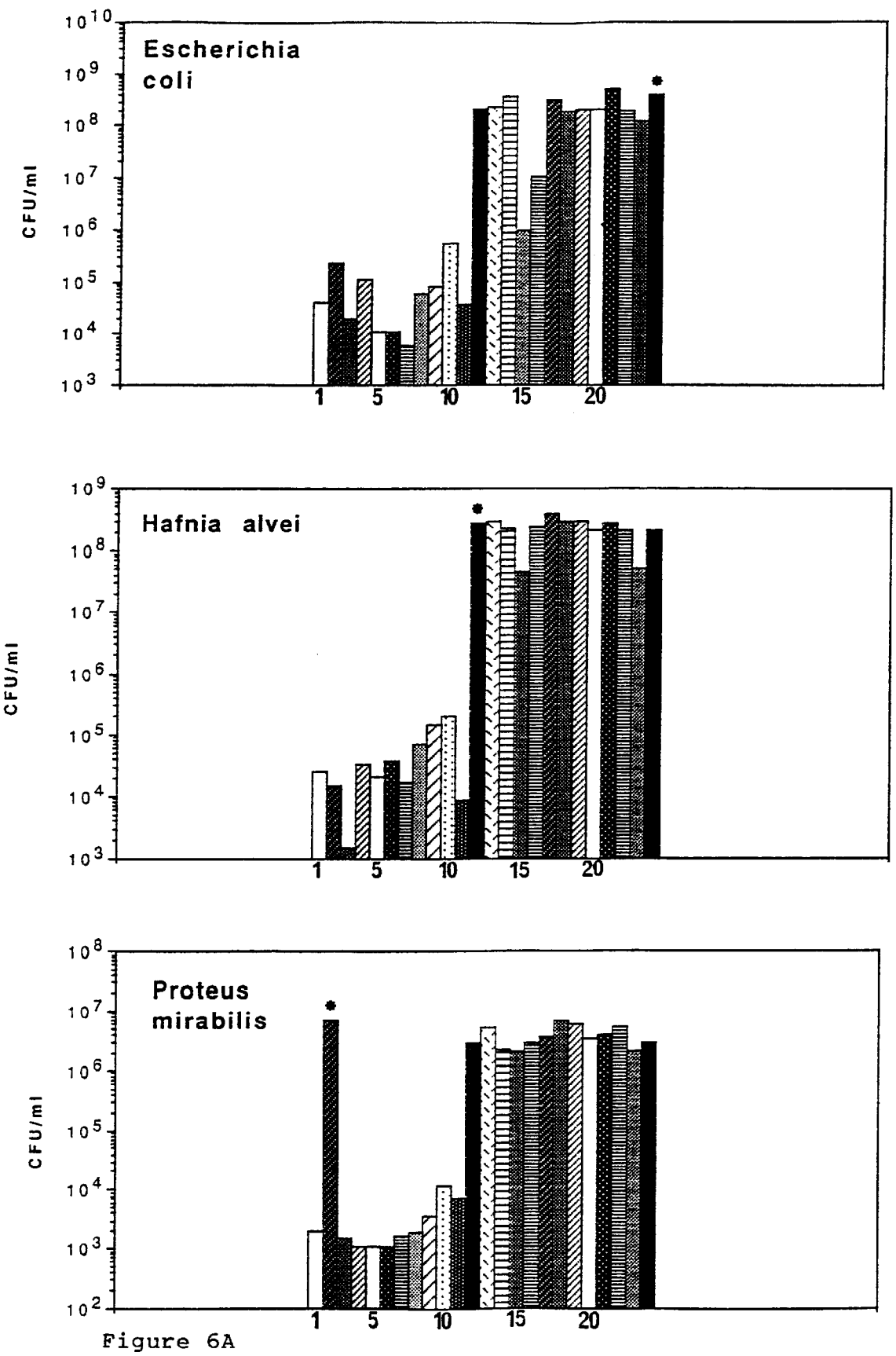
FIG. 6a shows the response of test bacteria to autoinducers of other bacteria (top, *E. coli*; middle, *Hafnia alvei*; bottom, *Proteus mirabilis*). Y-axes show CFU/ml and X-axes show (and also for FIGS. 6B, 6C, 6D and 6E) the test bacteria (1=control, serum/SAPI only—no autoinducer; 2=*Proteus mirabilis*; 3=*Pseudomonas aeruginosa*, 4=*Yersinnia entercolitica*; 5=*Morganella morganii*; 6=*Staphylococcus albus*; 7=*Staphylococcus aureus*; 8=*Streptococcus dysgalacticae*; 9=*Listeria monocytogenes*; 10=*Enterococcus faecalis*; 11=*Enterococcus faecium*; 12=*Hafnia alvei*; 13=*Klebsiella oxytoca*; 14=*Klibsiella pnuemoniae*; 15=*Acinetobacter lwoffii*; 16=*Xanthomanas maltophiia*; 17=*Citrobacter freundii*; 18=*Serratia marcescens*; 19=*Enterobacter sakazaki*; 20=*Enterobacter aerogenes*; 21=*Enterobacter cloacae*; 22=*Enterobacter agglomerans*; 23=*Salmonella enterica* Sv *Enteriditis*; 24=*Escherichia coli*)\*=autoinduction.
Figure 6B:
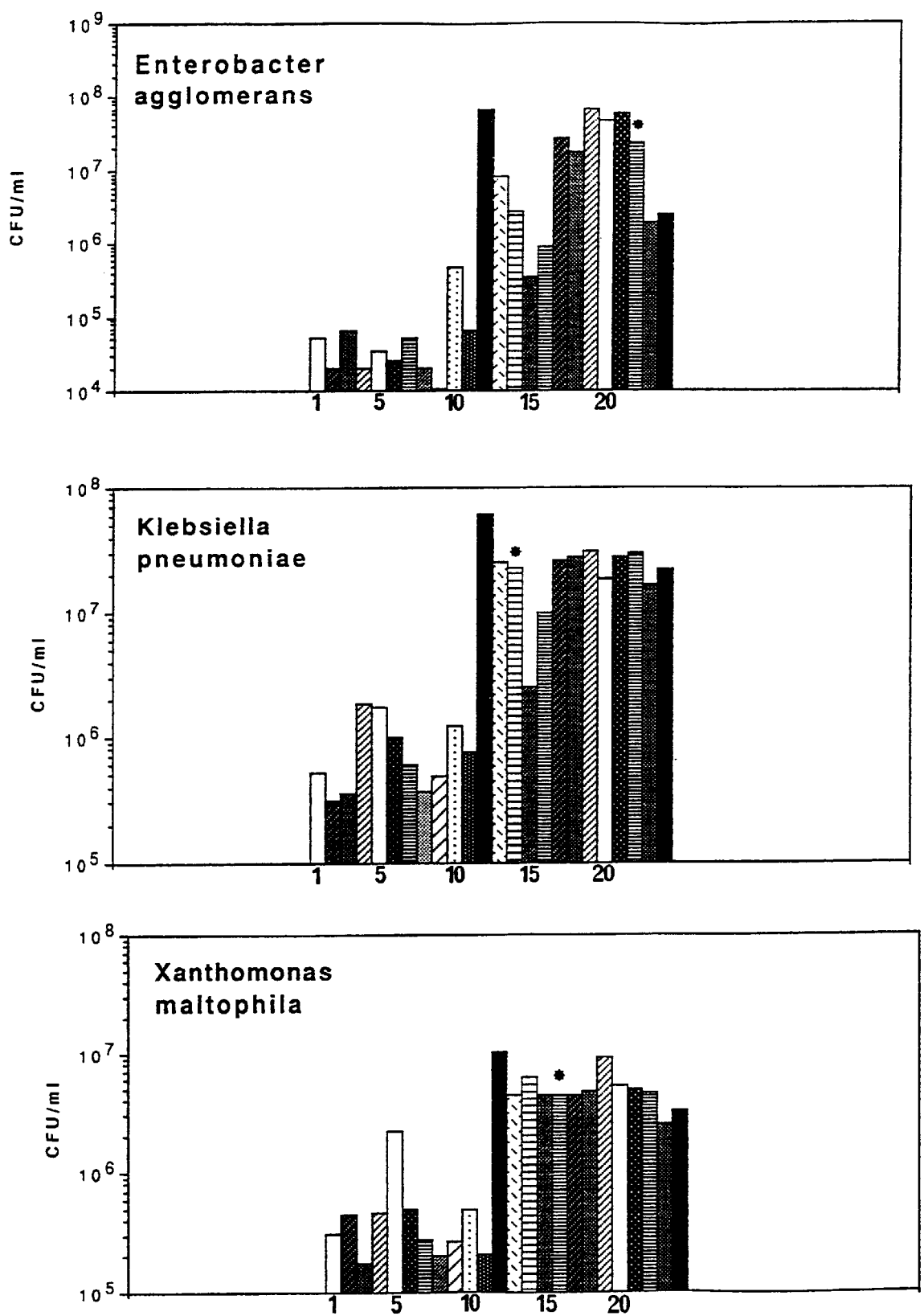
FIG. 6b shows effects of autoinducer from (top) *Enterobacter agglomerans*, (middle) *Klebsiella pneumoniae* and (bottom) *Xanthomonas maltophila*. Axes as for FIG. 6A.
Figure 6C:
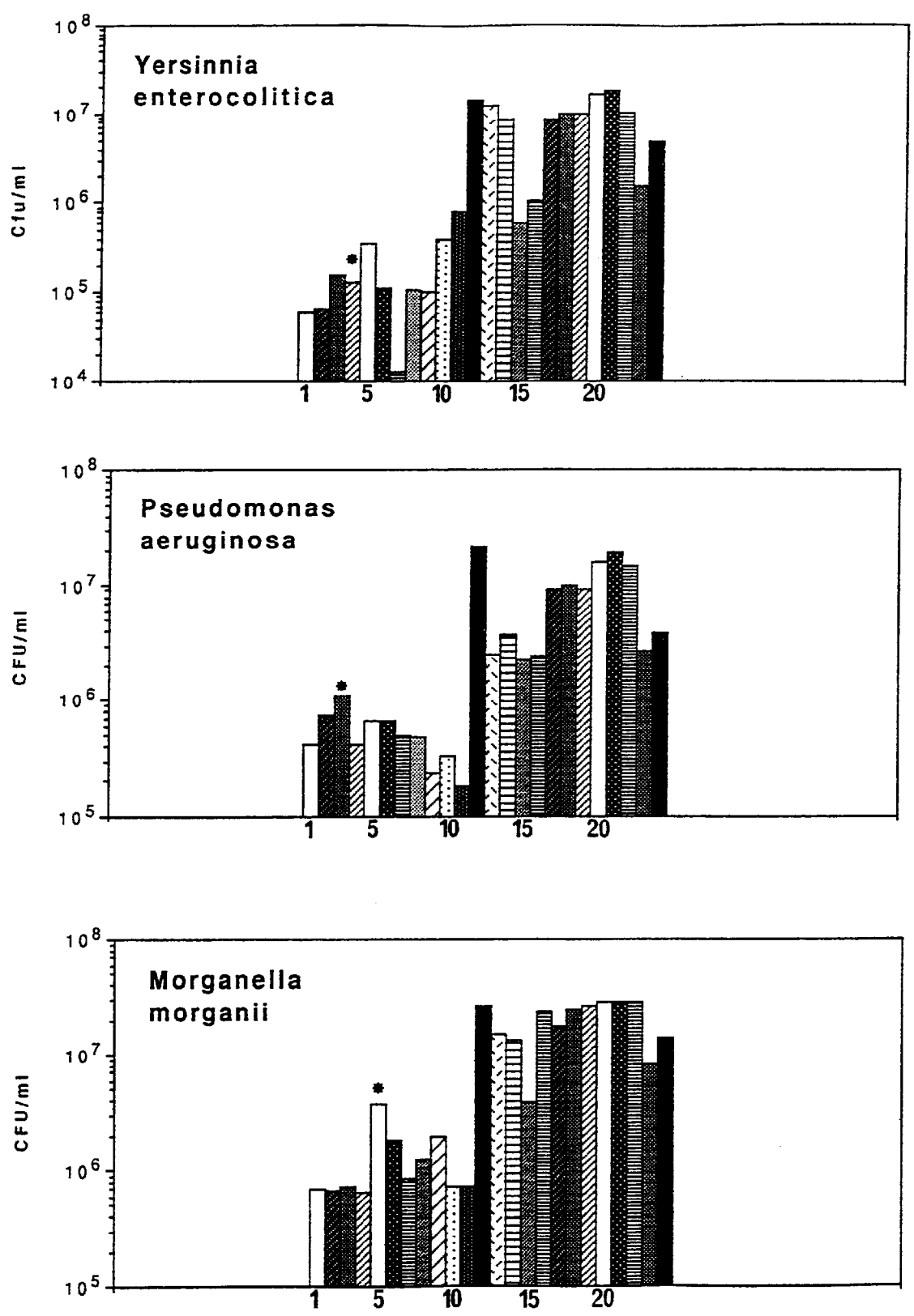
Figure 6D:
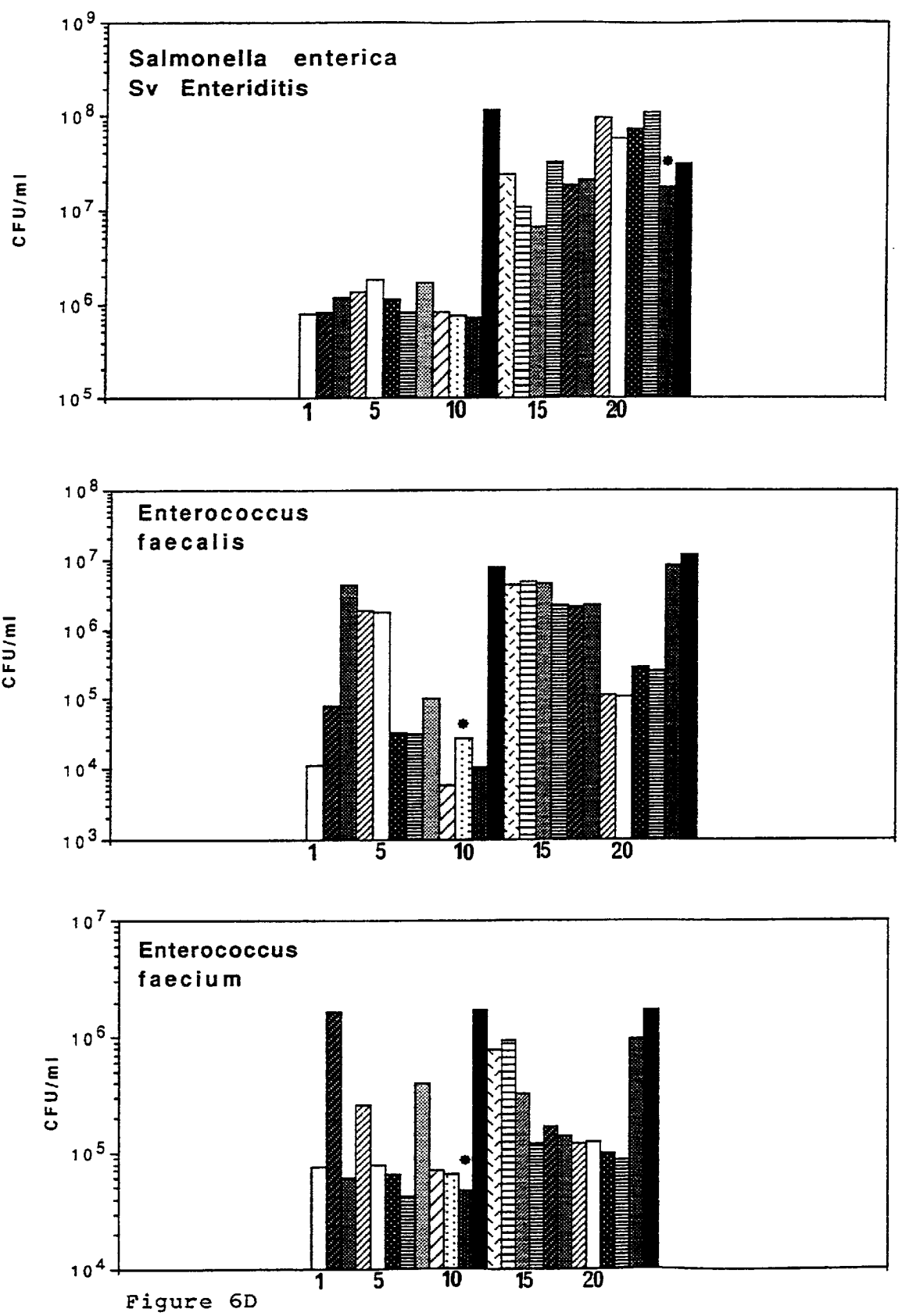
Figure 6E:
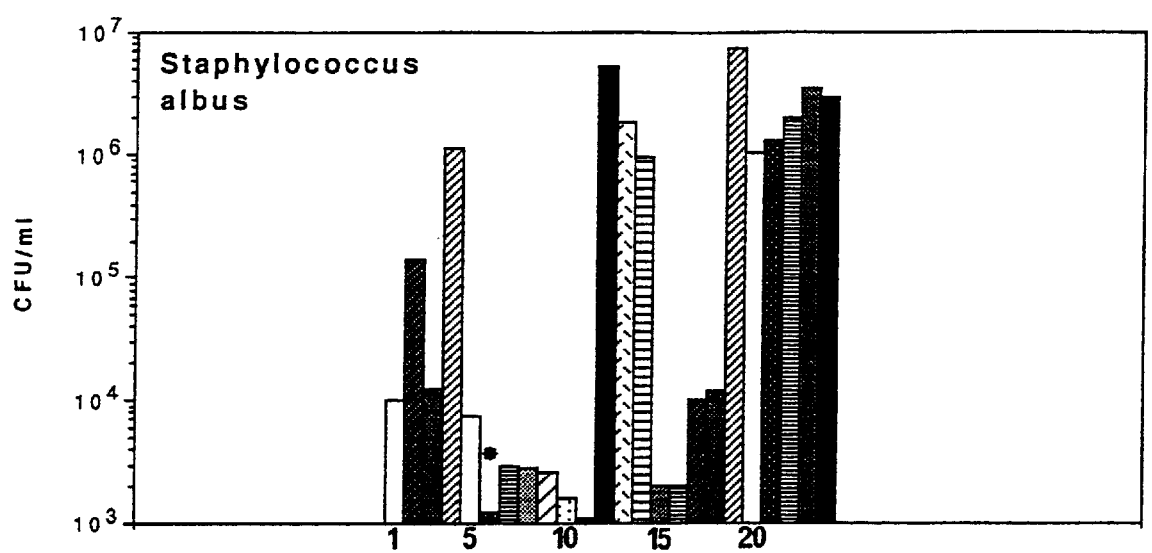

It has been shown that certain of these bacteria respond to norepinephrine (NE) and synthesise their own autoinducers, all of which are heat-stable low molecular weight molecules (less than 1000 Da) similar in size to the *E. coli* autoinducer (Table 4, FIG. 5).

These molecules are able to stimulate growth and autoinducer production both in *E. coli* and amongst each other, a similarity of action which suggests that they may share a similar chemical structure (FIGS. 5, 6A–6E).

Using the purification scheme (above) developed for the *E. coli* autoinducer it has also been possible to purify the corresponding activity from *Hafnia alvei*. The autoinducer from this organism, which shares with the *E. coli* molecule the same wide breadth of ability to signal across species boundaries, is also highly electronegative and reddish-pink in colour, although somewhat smaller (by around 100 Da, Superdex pep $V_e$ approx 31.5 ml).

Autoinducer Structural Analysis (see also Table 5, FIGS. 7A–7D, 8A, 8B)

Size

Dialysis, gel filtration chromatography and various forms of Mass Spectroscopy suggest a molecular weight of around 500 Da for the *E. coli* autoinducer. This molecular weight is too low to be indicative of a typical Gram positive peptide pheromone-type structure (which have variable molecular weights but which are usually very much greater than 1000 Da)

AI is not a homoserine lactone

However, while the *E. coli* autoinducer is of a similar size to certain of the N-acyl homoserine lactones, it differs from them in several important respects. Homoserine lactones are optimally produced in standard laboratory media predominantly during stationary phase, while synthesis of autoinducer occurs primarily in specialised media maximally during exponential growth. Homoserine lactones are inactivated by heating; in contrast, the *E. coli* autoinducer can be autoclaved without losing activity. Homoserine lactones are moderately hydrophobic, they partition into organic solvents and they bind to reverse phase columns; the *E. coli* autoinducer is very hydrophilic, and will not partition into organic solvents, or bind to reverse phase columns even after acidification. Most importantly, *E. coli* autoinducer does not display any activity in a homoserine lactone assay using *Agrobacterium tumefaciens* reporter strain (11).

These results strongly suggest that the *E. coli* autoinducer of growth is not a homoserine lactone.

The *E. coli* AI may be a highly modified, novel siderophore

Amino acid analysis has shown the unequivocal presence of serine in the *E. coli* autoinducer. The pink/red colouration and the growth enhancing properties of the autoinducer is suggestive of a siderophore, even though the breadth of cross species activity shown by the autoinducer is unprecedented amongst siderophores. Work with *E. coli* and *Salmonella typhimurium* 'iron-response' mutants which are defective in the genes responsible for the early steps in the synthesis of the enterochelin ferrisiderophore (entA and entB) are also unable to synthesise autoinducer, although they are still able to respond to AI given as a supplement. Further, evidence obtained with Salmonella strains with mutations in receptor proteins for catechol (and therefore enterochelin/siderophore) uptake systems (cir, iroN and fepA), and an *E. coli* mutant which is defective in the exbB gene (which encodes a protein involved in energising the cir, iroN and fepA siderophore receptors), suggest that a similar pathway of entry into the cell may also be taken by autoinducer. ICP Trace metal analysis of 16 mg of Step 3 purified autoinducer showed a significant presence of iron. However, the amounts of Fe detected (approximately 2% Fe w/w of AI) were lower than the 10% w/w ratio one would expect for a siderophore of 500 Da carrying one Fe iron of 55 Da. By association, these results suggests that the autoinducer is a siderophore. However, the following functional aspects of the autoinducer suggests against this:

Induction of siderophore synthesis is specific to conditions of iron starvation. Synthesis of the *E. coli* autoinducer is not induced in standard laboratory media under conditions of iron deficiency (such as addition of the iron chelator dipyridyl) which other labs have shown to result in the production of mg amounts of siderophore, and crucially, the molecule is still made in serum medium despite the addition of excess iron.

The autoinducer also appears to be very much more stable than the literature suggests:

enterochelin has a half-life of around 30 minutes at room temperature, the autoinducer has a half-life measured in weeks and months.

Enterochelin, a trimer of dihydoxybenzoylserine, can be acidifed without inactivation, is soluble in organic solvents, and forms white crystals when crystallised from ethanol. Autoinducer has none of these properties.

The presence of Fe within the autoinducer, the involvement of the entA and entB genes in AI synthesis, and involvement of siderophore receptors in AI uptake are strongly suggestive of a siderophore-type structure. However, many other aspects of AI structure and conditions of synthesis are atypical of siderophores. If the autoinducer is indeed a siderophore, it is unlike enterochelin, and indeed any siderophore described previously.

Trace metal analysis

Trace metal analysis with 16 micrograms of purified *E. coli* AI showed a higher than background amount of iron (molecular weight approx. 55 Da) (although less than one would expect with enterochelin—only around 2% weight of AI/weight of Fe ratios, instead of the 10% that would be expected for a molecule of MWt 500).

Other Properties of the *E. coli* Autoinducer

Although extremely stable to heat and prolonged storage, the AI is unstable to oxidation and extremes of pH (particularly acidity). Prolonged incubation with various degradative enzymes such ribonuclease, deoxyribonuclease, proteases (trypsin, pepsin, V8 protease, proteinase K), phosphatases (acid or alkaline) or phosphodiesterase is without effect. However, the autoinducer is inactivated by a bacterial sulphatase. The presence of sulphate groups would be consistent with the electronegativity of the autoinducer, and the observation that ammonium sulfate (but not equivalent mM concentrations of ammonium chloride, formate, acetate or bicarbonate) can stimulate growth and autoinducer production in our serum assay.

The *E. coli* autoinducer is highly electronegative. Analysis on anion exchange columns shows two discrete peaks of activity, indicating that the molecule exists in at least two negatively charged states.

Figure 7A:
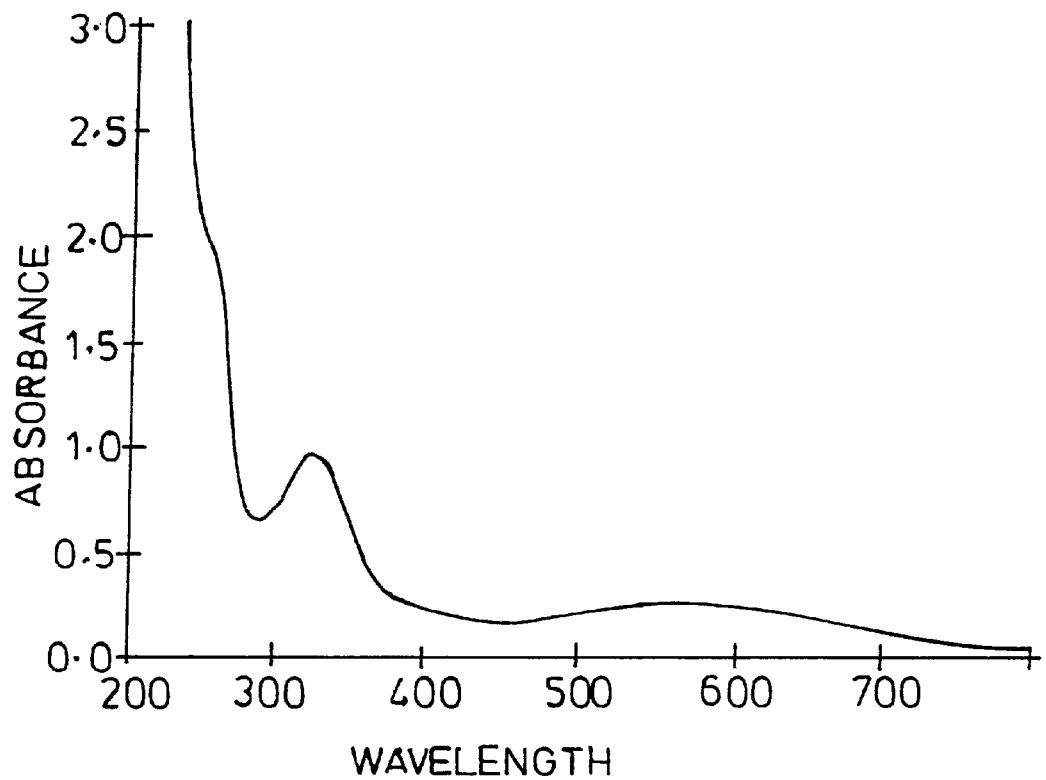
FIG. 7A shows the UV/Visible spectrum from 200–800 nm of (top) homogeneous (Step 3-purified) *E. coli* autoinducer (0.3 mg/ml) and (bottom) homogeneous *H. alvei* autoinducer (0.22 mg/ml). Absorption maxima are observed at <200 nm, 255 nm, 325 nm and around 500–550 nm.
Figure 7A:
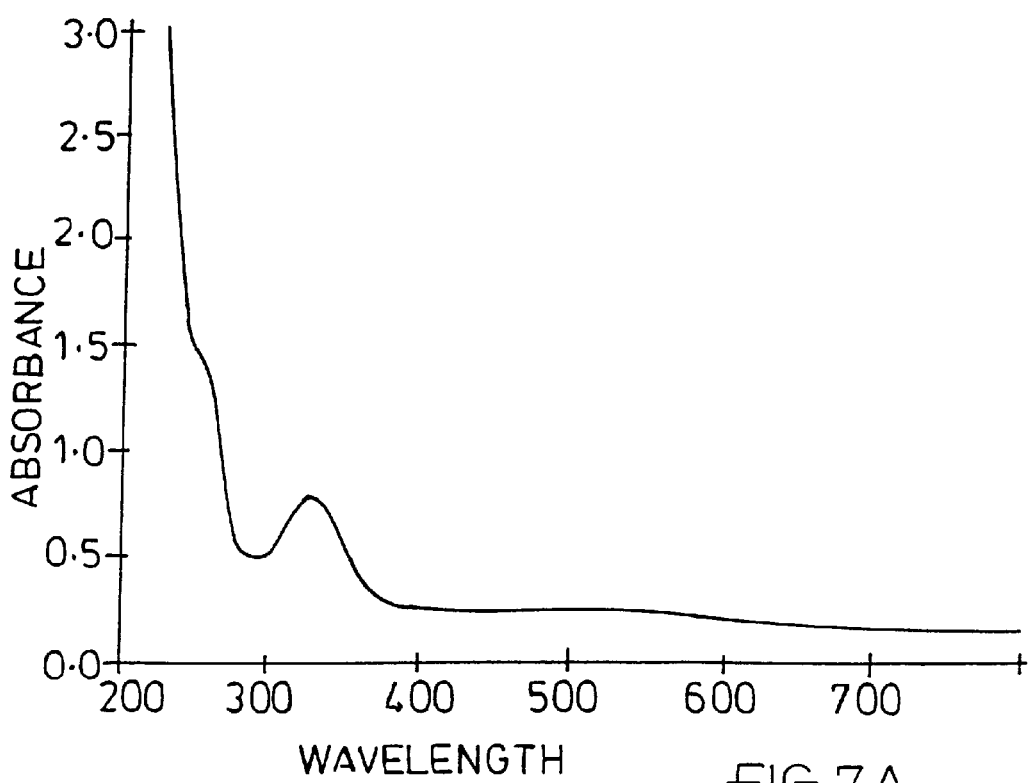
Figure 7B:
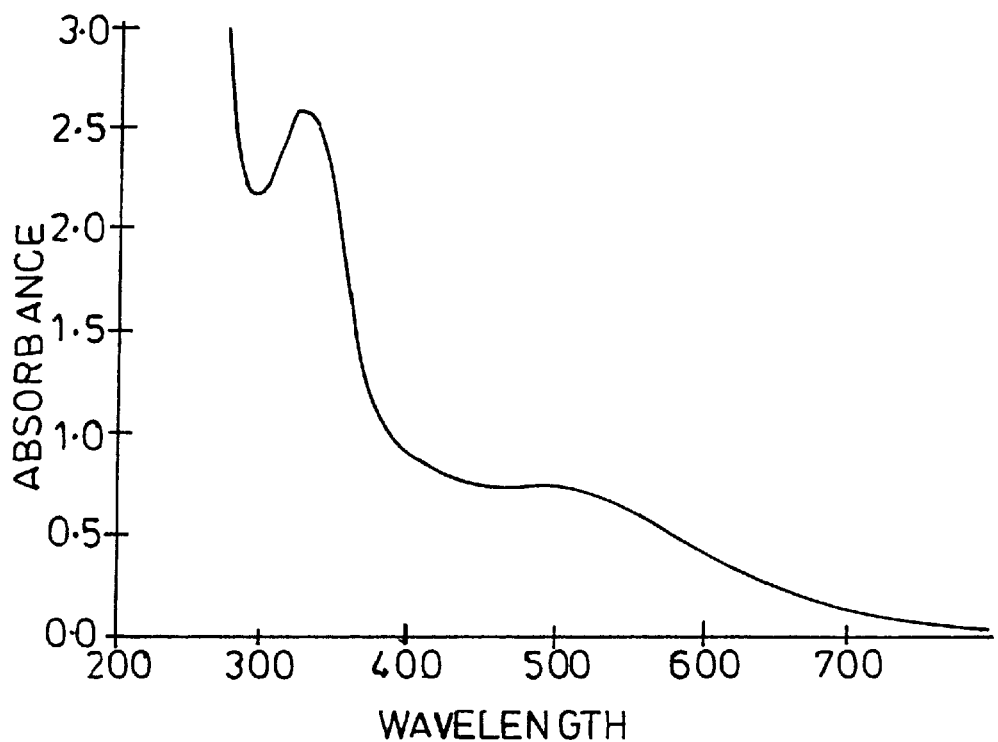
FIG. 7B shows the 200–800 nm absorption spectra for more concentrated, but less pure *E. coli* autoinducer (1 mg/ml) (top) and *H. alvei* autoinducer (0.7 mg/ml) (bottom). The materials shown are peak Step 2 Mono P fractions (approximately 50% pure).
Figure 7B:
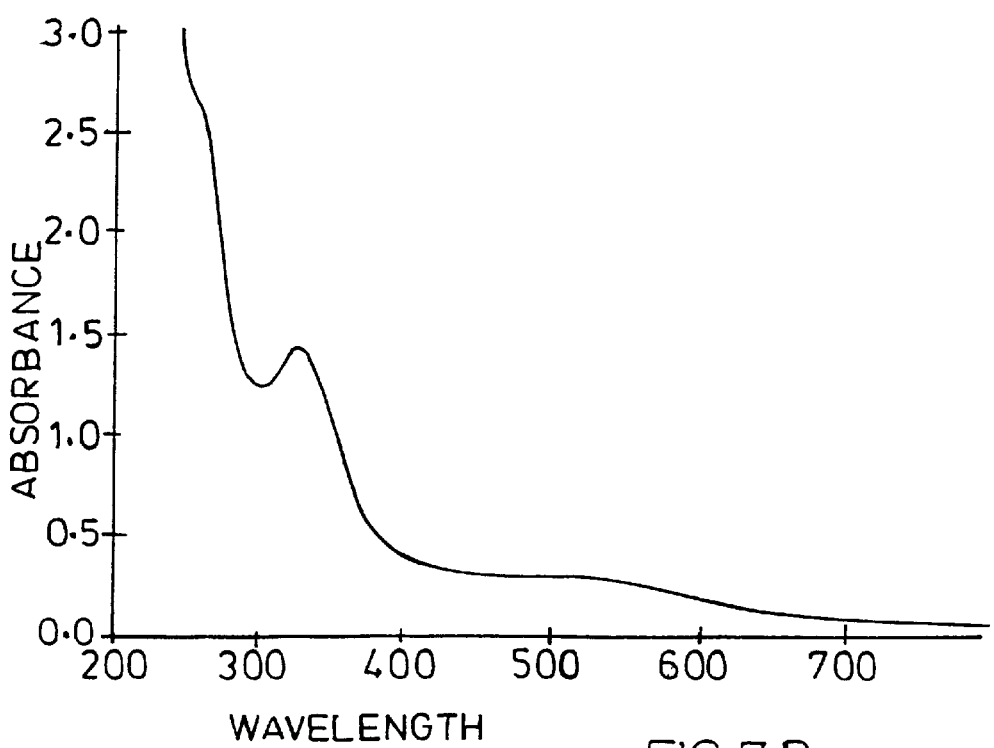

Preliminary UV/visible scans of purified *E. coli* and Hafnia autoinducers are shown in FIG. 7A. Absorbance spectra from more concentrated but somewhat less pure AI preparations (around 50% of total components) of both species are also shown (FIG. 7B). Absorption maxima are observed at <200 nm, 255 nm, 325 nm and around 500–550 nm. All preparations of the *E. coli* and Hafnia autoinducer to date have been reddish-pink in colour; purification of the corresponding negative control supernatants (which contain no autoinducer) are not red. This colouration is pH-dependent, and acidification (to less than pH 4) results in de-colourisation (reversible upon re-neutralisation). Despite the apparent colour of the autoinducer, the visible spectrum of the molecule is rather indeterminate.

The absorbance spectra of the *E. coli* and Hafnia autoinducers are not suggestive of a simple peptide structure. However, the autoinducer does stain positively with ninhydrin, and amino acid analysis of homogeneous *E. coli* autoinducer from two separate purifications clearly shows that an amino acid, serine, is a structural component of the molecule. No significant amount of any amino acid other than serine was detectable in the amino acid analyses.

Mass spectrometry analysis of the autoinducer has so far produced somewhat perplexing data. This is a summary of the spectra we have obtained so far. We have restricted our analysis to Step 2 (Mono P anion exchange) and Step 3 (Superdex peptide gel filtration) purified autoinducer.

Positive detection mode ESMS of highly concentrated Step 2 autoinducer consistently shows two major ion peaks of 407 and 465 Da. The 465 ion also occasionally occurs in a $Na^+$-bound form (not shown). The 465 Da ion is also visible as a 464 Da molecule in negative ion detection mode Fast Atom Bombardment (FAB) MS. The 407 ion is undetectable in negative mode FAB MS. An additional 514 Da ion is also visible as a major species, and a 692 ion as a minor species, in negative FAB MS of Step 2 autoinducer. These ion sizes are within the range of estimates of autoinducer molecular weight indicated by other forms of analysis.

Gel filtration fractionation of Step 2 autoinducer reveals around 9 discrete UV-absorbing peaks; autoinducer activity is only associated with the peak eluting around 28.5 ml (FIG. 4). However, positive mode ES MS (not shown), and negative mode FAB MS of Step 3 autoinducer peak fail to show the presence of any of the 407, 465 and 514 ions. Instead, with negative mode FAB MS a strange-looking very low molecular weight polymeric molecular species is observed, with ion sizes ranging from around 100 Da to 400 Da, and a repeating interval of 15 Da. No higher molecular weight species are observed. When this material is mixed with Step 2 autoinducer, instead of seeing any peak accentuation, flight of the 464, 514 and 692 ions is actually suppressed.

It is possible that the ions seen in the Step 2 autoinducer are derived from the 8 other non-autoinducer molecules present in this preparation. However, ES and FAB analysis of concentrated preparations of each of these peaks still fails to reveal the presence of the 407, 465, 514 and 692 ions.

It is possible that the autoinducer has not been visualised using MS techiques (above).

However, the results obtained show a mixture of aliphatic di-ethanol-type groups (probably derived from TEAB bound as counterion to the autoinducer) and a much weaker aromatic signal, possibly derived from the autoinducer itself.

TABLE 1

| Culture | |
|---|---|
| Strain | *E. coli* O157:H7 |
| Medium | SAPI minimal medium + 30% bovine serum + 1% (v/v) autoinducer (or 50 μm nor-epinephrine) |
| Conditions | static culture, 5% $CO_2$, 24 hours |
| Recovery | centrifuge, filter-sterilise supernatants, lyophilise, re-dissolve in distilled water at 1/8 original volume |
| Purification | |
| Step 1 | Superdex 30 gel-filtration (size exclusion) chromatography superdex 30 pg (Pharmacia) column (2.6 × 65 cm) equilibrated in 100 mM $NH_4HCO_3$ AI elution volume ($V_e$) = 220 – 330 ml |

TABLE 1-continued

| Step 2 | Mono P anion exchange chromatography Mono P 5/5 (Pharmacia) column linear gradient elution using the volatile salt TEAB (triethyl ammonium bicarbonate) AI elutes between 500 and 700 mM TEAB |
|---|---|
| Step 3 | Superdex peptide gel filtration (size exclusion) chromatography Superdex peptide column (Pharmacia) (1 × 60 cm) equilibrated in 200 mM TEAB AI elution volume ($V_e$) = 28.5 mM |

TABLE 2

| | | Stability of AI | |
|---|---|---|---|
| | | Crude | Purified |
| boiling (45 minutes) | | 100% | 100% |
| autoclaving (25 minutes) | | 100% | 100% |
| lyophilisation | | 100% | 100% |
| acid | pH 5 (24 hours) | 100% | 100% |
| | pH 1 (1 hour) | 30% | <10% |
| alkali | pH 11 (24 hours) | 100% | 100% |
| | pH 14 (1 hour) | 0% | 0% |
| storage* | −20° C. | >14 months | >5 months |
| | 4° C. | >9 months | >3 months |
| | 20° C. | >3 months | 6 weeks |

*storage data indicate the period of time tested so far after which 100% of acitivity remains.

TABLE 3

Transposon mutants in *E. coli* which fail to respond to NE or AI

| | Phenotypic response in SAPI/30% | Mutagenesis Strategy | |
|---|---|---|---|
| Mutant Type | serum media | TnphoA[a] | STM[b] |
| Class I | reduced for NE/reduced for AI | 10 | 12 |
| Class II | reduced for NE/negative for AI | 2 | 2 |
| Class III | negative for NE/reduced for AI | 0 | 3 |
| Class IV | negative for NE/negative for AI | 0 | 9 |
| Class V | WT for NE/reduced or negative for AI | 0 | 7 |

TABLE 4

| Species | Control | Response to NE | Response to *E. coli* AI | Respsonse to own conditioned medium* |
|---|---|---|---|---|
| Enterobacteriaceae | | | | |
| *Acinetobacter lwoffii* | $1.0 \times 10^4$ | $2.9 \times 10^7$ | $8.6 \times 10^6$ | $3.2 \times 10^7$ |
| *Citrobacter freundii* | $1.9 \times 10^6$ | $3.5 \times 10^7$ | $2.4 \times 10^6$ | $1.2 \times 10^7$ |
| *Enterobacter aerogenes* | $3.2 \times 10^8$ | $5.5 \times 10^8$ | $5.1 \times 10^8$ | $4.0 \times 10^8$ |
| *Enterobacter agglomerans* | $2.9 \times 10^4$ | $6.1 \times 10^6$ | $1.1 \times 10^6$ | $2.9 \times 10^6$ |
| *Enterobacter cloacae* | $7.2 \times 10^6$ | $1.1 \times 10^8$ | $1.7 \times 10^7$ | $5.8 \times 10^7$ |
| *Enterobacter sakazaki* | $3.0 \times 10^6$ | $4.1 \times 10^7$ | $2.5 \times 10^6$ | $4.9 \times 10^6$ |
| *Escherichia coli* | $7.5 \times 10^4$ | $5.9 \times 10^8$ | $2.3 \times 10^8$ | $2.3 \times 10^8$ |
| *Hafnia alvei* | $1.2 \times 10^4$ | $3.7 \times 10^8$ | $3.0 \times 10^8$ | $2.9 \times 10^8$ |
| *Klebsiella oxytoca* | $4.2 \times 10^4$ | $1.6 \times 10^8$ | $6.9 \times 10^7$ | $9.5 \times 10^7$ |
| *Klebsiella pneumoniae* | $3.1 \times 10^4$ | $6.7 \times 10^7$ | $1.6 \times 10^7$ | $2.2 \times 10^7$ |
| *Morganella morganii* | $3.7 \times 10^4$ | $1.6 \times 10^7$ | $7.4 \times 10^7$ | $1.9 \times 10^5$ |
| *Proteus mirabilis* | $1.1 \times 10^3$ | $1.0 \times 10^7$ | $4.1 \times 10^6$ | $6.9 \times 10^6$ |
| *Salmonella enterica* sv Enteriditis | $7.5 \times 10^5$ | $1.0 \times 10^8$ | $3.3 \times 10^7$ | $1.7 \times 10^7$ |
| *Serratia marcescens* | $8.5 \times 10^7$ | $3.4 \times 10^8$ | $2.9 \times 10^8$ | $3.5 \times 10^8$ |
| *Yersinia entercolitica* | $4.2 \times 10^4$ | $1.7 \times 10^8$ | $5.2 \times 10^6$ | $1.3 \times 10^5$ |

TABLE 4-continued

| Species | Control | Response to NE | Response to E. coli AI | Respsonse to own conditioned medium* |
|---|---|---|---|---|
| Other Gram negatives | | | | |
| Pseudomonas aeruginosa | $3.7 \times 10^4$ | $2.1 \times 10^7$ | $4.7 \times 10^6$ | $9.5 \times 10^5$ |
| Xanthomonas maltophilia | $1.7 \times 10^5$ | $2.1 \times 10^6$ | $1.6 \times 10^6$ | $4.5 \times 10^6$ |
| Gram positives | | | | |
| Enterococcus faecalis | $5.0 \times 10^5$ | $5.5 \times 10^6$ | $1.4 \times 10^7$ | $2.8 \times 10^5$ |
| Enterococcus faecium | $2.1 \times 10^5$ | $5.6 \times 10^6$ | $1.5 \times 10^7$ | $4.8 \times 10^5$ |
| Listeria monocytogenes | $2.5 \times 10^5$ | $3.5 \times 10^6$ | $1.2 \times 10^6$ | $1.8 \times 10^4$ |
| Staphylococcus albus | $1.1 \times 10^3$ | $1.5 \times 10^7$ | $5.5 \times 10^5$ | $4.5 \times 10^2$ |
| Staphylococcus aureus | $3.2 \times 10^5$ | $5.7 \times 10^5$ | $3.0 \times 10^5$ | $1.9 \times 10^5$ |
| Streptococcus dysgalactiae | $2.0 \times 10^7$ | $2.4 \times 10^6$ | $2.8 \times 10^4$ | $2.9 \times 10^6$ |
| Streptococcus sanguis | $2.1 \times 10^4$ | $1.1 \times 10^4$ | $1.6 \times 10^4$ | $1.0 \times 10^4$ |

Results are given as CFU/ml

TABLE 5

| Properties of the E. coli autoinducer (AI) | |
|---|---|
| Small | <500 Da |
| Novel | Not an N-acyl homoserine lactone or peptide pheremone |
| Synthesis | Synthesised in exponential phase growth in "stressful" media |
| Stability | Very stable to heat, lyophilisation and prolonged storage (dried or in solution) |
| Absorbance | Slight absorbance at 280 and 206–212 nm |
| Colour | Red |
| Specificity | Stimulates growth of a range of other bacteria |
| Homology | Functionally and possibly structurally similar to molecules made by a range of other bacteria |

What is claimed is:

1. A method for inducing bacterial growth, the production of bacterial toxins or the production of bacterial adhesions, comprising the steps of:
   i) contacting a sample containing bacteria with a bacterial autoinducer having the following properties:
      a) it is produced in response to noradrenaline in serum SAPI medium;
      b) it is heat stable;
      c) it is stable to lyophilisation;
      d) it has a negative charge;
      e) it is polar;
      f) it is hydrophilic;
      g) it will not partition into organic solvents;
      h) it is capable of binding positively charged metal ions; and
      j) it has a molecular weight of about 300–1500 daltons; and
   ii) culturing said bacteria, thereby inducing bacterial growth or producing bacterial toxins or bacterial adhesions.

2. A method according to claim 1, said bacterial autoinducer further having the following properties:
   i) it has absorbtion maxima at 255, 325 and 500–550 nm; and
   ii) it is stable in prolonged storage in a dried state and/or in solution.

3. A method according to claim 1, said bacterial autoinducer further having the following properties:
   i) it is produced in substantially smaller quantities by bacteria grown in LURIA broth, Tryptone, soy broth, M9 minimal medium and Davis-Mingioli minimal medium than by the same bacteria grown in serum SAPI medium;
   ii) it has a reddish-pink colour, reversibly decolorisable by reducing the pH to <4;
   iii) it contains seine;
   iv) its synthesis involves the entA and entB gene products;
   v) its synthesis is not stimulated by conditions of Fe starvation;
   vi) it is synthesised in conditions of excess Fe;
   vii) its entry into bacteria occurs via a tonB dependent receptor;
   viii) it is inactivated by oxidation;
   ix) it is inactivated by extreme pH; and
   x) it is resistant to degradation by ribonuclease, deoxyribonuclease, trypsin, pepsin, V8 protease, proteinase K, acid phosphates, alkaline phosphates and phosphodiesterase.

4. A method according to claim 1, said bacterial autoinducer being an E. coli, Salmonella or Hafnia alvei autoinducer.

5. A method according to claim 1, said bacterial autoinducer being an Enterobacter agglomeran or Klebsiella pneumoniae autoinducer.

6. A method according to claim 1, the bacteria in said sample containing bacteria being selected from the group consisting of E. Coli, Salmonella$_2$ Hafnia alvei, Proteus mirabilis, Pseudomonas aeruginosa, Yersinnia entercolitica, Morganella morganii, Staphylococcus albus, Staphylococcus aureus, Streptococcus dysgalacticae, Listeria monocytogenes, Enterococcus faecalis, Enterococcus faecium, Klebsiella oxytoca, Klibsiella pneumoniae, Acinetobacter lwoffi, Xanthomanas maltophiia, Citrobacter freundii, Serratia marcescens, Enterobacter sakazaki, Enterobacter aerogenes, Enterobacter cloacae and Enterobacter agglomerans.

7. A method according to claim 1, said bacterial autoinducer having been isolated and purified by a method comprising the steps of:
   i) collecting a sample containing an autoinducer;
   ii) fractioning the sample to isolate fractions corresponding to molecular weights of approximately 300–1500 Daltons; and
   iii) eluting the isolate of (ii) on an anion-exchange chromatographic column and selecting the fraction containing the autoinducer.

8. A method according to claim 7, wherein the sample being collected is from a culture containing bacteria and the autoinducer.

9. A method according to claim 7, wherein the fractionating step further comprises performing a size exclusion gel filtration using a buffer of approximately 100 mM ammonium bicarbonate, pH 8.0, and the eluting step further comprises performing an anion exchange purification on an anion exchange column and triethylammonium bicarbonate.

10. A method according to claim 7, wherein the fractionating step further comprises performing a size exclusion gel filtration using a buffer of approximately 20 mM potassium phosphate containing 1500 mM NaCl, pH 7.4, and the eluting step further comprises performing an anion exchange purification on an anion exchange column and NaCl gradient.

11. A method according to claim 7, wherein the bacterium from which the autoinducer is derived is E. Coli, Salmonella or Hafnia alvei.

12. A method according to claim 7, wherein the bacterium from which the autoinducer is derived is Enterobacter agglomerous, or Klebsiella pneumoniae.

* * * * *